(12) United States Patent
Crislip Wilkinson

(10) Patent No.: US 7,591,811 B2
(45) Date of Patent: *Sep. 22, 2009

(54) DIAPER WITH LEGS

(76) Inventor: Lisa Diane Crislip Wilkinson, 373 Spring St., Spencer, TN (US) 38585

(*) Notice: Subject to any disclaimer, the term of this patent is extended or adjusted under 35 U.S.C. 154(b) by 472 days.

This patent is subject to a terminal disclaimer.

(21) Appl. No.: 11/153,444

(22) Filed: Jun. 16, 2005

(65) Prior Publication Data

US 2005/0222553 A1    Oct. 6, 2005

Related U.S. Application Data

(63) Continuation-in-part of application No. 10/791,849, filed on Mar. 4, 2004, now Pat. No. 6,926,702.

(51) Int. Cl.
*A61F 13/20* (2006.01)

(52) U.S. Cl. ............... 604/385.25; 604/385.01; 604/385.21; 604/385.24; 604/385.26; 604/385.27; 604/385.29; 604/385.3; 604/346; 604/358; 2/75; 2/78.1; 2/78.2; 2/78.3; 2/78.4; 2/79; 2/80; 2/82; 2/111

(58) Field of Classification Search ........... 604/385.25, 604/385.01, 385.3, 385.21, 385.24, 385.26, 604/385.27, 385.29, 293, 346, 358, 361, 604/385.03; 2/78.1, 78.2, 78.3, 78.4, 79, 2/75, 80, 82, 111, 404, 67, 407, 100, 101, 2/116, 117, 135, 400, 109, 113, 228, 238, 2/242

See application file for complete search history.

(56) References Cited

U.S. PATENT DOCUMENTS

| | | | | |
|---|---|---|---|---|
| 2,763,009 A | * | 9/1956 | Blatt | 450/104 |
| 2,983,927 A | * | 5/1961 | McCann | 4/309 |
| 3,094,990 A | * | 6/1963 | Neilson | 2/400 |
| 4,936,840 A | | 6/1990 | Proxmire | |
| 5,103,501 A | * | 4/1992 | Meisels | 2/113 |
| 5,389,093 A | * | 2/1995 | Howell | 604/361 |
| 5,502,842 A | * | 4/1996 | Wagner | 2/67 |
| 5,916,206 A | | 6/1999 | Otsubo et al. | |
| 5,921,974 A | * | 7/1999 | Kikuchi | 604/385.24 |

(Continued)

FOREIGN PATENT DOCUMENTS

JP    11-290377    10/1996

(Continued)

*Primary Examiner*—Tatyana Zalukaeva
*Assistant Examiner*—Ginger T Chapman
(74) *Attorney, Agent, or Firm*—Richard C. Litman

(57) ABSTRACT

A diaper with legs is a lower torso garment worn by a user to retain excreted waste matter. The diaper may have fasteners to close the waist and legs, or may be of the pull-on type. The diaper includes a flat sheet wrapped around the torso with legs extending from the sides of the sheet. A front waist arch and a rear waist arch are disposed at an upper portion of the edges of the sheet. The arches extend the height of the diaper in front and back. An elastic material is disposed at the waist arches, at the junction between the legs and the central portion of the diaper, and at the end of the legs. The elastic material disposed at the end of the legs and at the junction between the legs and the central portion provides double leak protection at the legs.

30 Claims, 6 Drawing Sheets

U.S. PATENT DOCUMENTS

| | | | |
|---|---|---|---|
| 6,079,050 A * | 6/2000 | Hooper-Jackson | 2/78.1 |
| 6,156,024 A | 12/2000 | Schulte et al. | |
| 6,210,386 B1 | 4/2001 | Inoue | |
| 6,328,724 B1 | 12/2001 | Ronnberg et al. | |
| 6,482,196 B1 * | 11/2002 | Hisada | 604/385.3 |
| 6,520,944 B1 | 2/2003 | Jonbrink | |
| 6,926,702 B1 * | 8/2005 | Wilkinson | 604/385.01 |
| 7,314,967 B2 * | 1/2008 | Ashton et al. | 604/368 |
| 2002/0165518 A1 | 11/2002 | Datta et al. | |
| 2002/0183706 A1 * | 12/2002 | Valentin et al. | 604/385.01 |
| 2003/0149418 A1 | 8/2003 | Katz | |
| 2003/0158532 A1 | 8/2003 | Magee et al. | |
| 2003/0164136 A1 | 9/2003 | Klofta et al. | |
| 2003/0181883 A1 | 9/2003 | Olson et al. | |
| 2003/0199841 A1 | 10/2003 | Asthon et al. | |
| 2003/0199844 A1 | 10/2003 | La Von et al. | |
| 2003/0208171 A1 * | 11/2003 | Zehner et al. | 604/358 |
| 2003/0212378 A1 | 11/2003 | Kuen et al. | |
| 2003/0220626 A1 | 11/2003 | Karami | |
| 2003/0225385 A1 | 12/2003 | Glaug et al. | |
| 2003/0229327 A1 | 12/2003 | Imsangjan et al. | |
| 2003/0229329 A1 * | 12/2003 | Mercier et al. | 604/394 |
| 2004/0002690 A1 | 1/2004 | Miyamoto | |
| 2004/0002691 A1 | 1/2004 | Popp et al. | |
| 2005/0256473 A1 * | 11/2005 | Feldkamp et al. | 604/378 |

FOREIGN PATENT DOCUMENTS

| | | |
|---|---|---|
| JP | 2003-38554 | 2/2003 |
| JP | 2003-88262 | 3/2003 |
| JP | 2003-199778 | 7/2003 |
| JP | 2003-210518 | 7/2003 |

* cited by examiner

DIAPER WITH LEGS

CROSS-REFERENCE TO RELATED APPLICATION

This application is being filed as a Continuation-In-Part of U.S. patent application Ser. No. 10/791,849, filed Mar. 4, 2004, now U.S. Pat. No. 6,926,702.

BACKGROUND OF THE INVENTION

1. Field of the Invention

The present invention relates to disposable diapers, and more particularly to a diaper with legs. The diaper may have reclosable fasteners about the waist and legs, or may be of the pull-on type without fasteners.

2. Description of the Related Art

Absorbent articles for the lower torso, such as diapers, pull-on diapers and pull-on pants, are used to capture waste matter for infants and those who cannot control their bodily functions. Absorbent articles have made life cleaner and easier for those who wear the articles and their caregivers. These absorbent articles, however, are not entirely problem free. There are times when body exudates seep through the openings of the absorbent article, such as at the leg openings and the waist opening. A diaper is therefore desired that can contain waste matter that may leak out the openings of the diaper.

A number of pant-like absorbent articles have been developed to aid is retaining waste matter excreted by the body. U.S. Patent Publication Number 2002/0165518, published on Nov. 7, 2002, describes a pant-like, prefastened, disposable absorbent article that reduces leakage when worn as pants rather than a diaper. In one embodiment, the absorbent article has a pair of elastic leg members that are adapted to fit about the legs of a wearer. The leg members maintain contact with the legs and reduce or eliminate leaks. The absorbent article has an absorbent core with a pocket defined therein to receive and retain body exudates. Additionally, the absorbent article may have a containment flap disposed near the pocket to provide a barrier to the lateral flow of body excretions.

U.S. Patent Publication Number 2003/0181883, published on Sep. 25, 2003, describes a garment-like absorbent article. The article is a pant-like article that functions like underwear. The article has a pair of leg openings. The length of the outer cover of the article, measured from the front waist edge to the rear waist edge can be shorter then other bulkier garments so the article can be worn without being visible over the waistline of lower torso garments.

U.S. Pat. No. 5,916,206, issued to Ostubo et al. on Jun. 29, 1999, describes an absorbent pant-like undergarment that utilizes elastic elements to prevent leaks. The pants-type undergarment has a pair of leg openings to configure the garment into pants or a brief-like shape. U.S. Pat. No. 6,210,386, issued to Inoue on Apr. 3, 2001, describes a disposable pull-on, pant-type undergarment having elastic auxiliary flaps to secure the garment to the waist and aid in disposal of the garment. U.S. Pat. No. 6,328,724, issued to Ronnberg et al. on Dec. 11, 2001, describes an absorbent article having longitudinal side flaps for retaining liquid within the absorbent article.

U.S. Pat. No. 6,482,196, issued to Hisada on Nov. 19, 2002, describes disposable undergarment pants combined with a belly protector. The undergarment has a front body joined to a rear body to define both a tubular waist configuration at the top of the undergarment and leg openings at the bottom of the undergarment. Elastic is integrated into both the belly protector and the pants section of the undergarment.

U.S. Patent Publication Number 2003/0199841, published on Oct. 23, 2003 to Ashton et al., describes an absorbent article having article retention zones dependent on static friction. One embodiment shows a pant-like absorbent article. Japanese Patent Number 2003-210518, published on Jul. 29, 2003, shows a disposable pant-type diaper having legs. Japanese Patent Number 2003-38554, published on Feb. 5, 2003, shows a pant-type disposable diaper having a penis-receiving zone.

Some absorbent articles have been developed that utilize leg cuffs. U.S. Patent Publication Number 2003/0208171, published on Nov. 6, 2003, describes an absorbent article with self-forming seals. The article fits like pants having seals at natural body hinge points of a wearer and in-captured elastic leg cuffs. The leg cuffs extend from the absorbent core of the diaper article and provide targeted stretch and recovery as the leg moves.

U.S. Patent Publication Number 2003/0158532, published on Aug. 21, 2003, describes a disposable absorbent article for the lower body. The article may have barrier cuffs or gasketing leg cuffs disposed on a portion of the article that faces the body. The cuffs may help in preventing leaks. U.S. Patent Publication Number 2004/0002690, published on Jan. 1, 2004, describes a disposable absorbent article having elasticized outer leg cuffs. The gasket cuff contains a sleeve that holds elastic material to provide a seal with the leg.

U.S. Pat. No. 6,156,024, issued to Schulte et al. on Dec. 5, 2000, describes an absorbent article having lotioned leg cuffs. Japanese Patent Number 2003-88262, published on Mar. 25, 2003, describes a pet diaper. Japanese Patent Number 11-290377, published on Oct. 26, 1999, shows a pants-shaped disposable diaper having elastic members on a front panel and a back panel. Japanese Patent Number 2003-199778, published on Jul. 15, 2003, shows a diaper cover having a pocket for holding a urine-taking pad.

Absorbent articles utilizing a number of absorbent core components are described in U.S. Patent Publication Number 2003/0199844, published on Oct. 23, 2003 (disposable absorbent article for a lower body, having pockets to store multiple replaceable absorbent core components) and U.S. Patent Publication Number 2003/0225385, published on Dec. 4, 2003 (an absorbent article having longitudinally arranged multiple core components).

Some absorbent articles have been developed that utilize fastener elements to retain the absorbent article on a wearer. U.S. Patent Publication Number 2004/0002691, published on Jan. 1, 2004, describes absorbent pants having an optimized leg opening shape designed to transfer stress away from a fastener element and minimize the possibility of the fastener disengaging.

U.S. Pat. No. 4,936,840, issued to Proxmire on Jun. 26, 1990, describes a method of reducing waist droop in a disposable diaper. The diaper has landing zones on a front panel and ear fasteners on a back panel. The method requires the landing zones to be oriented on the front panel so tensile stresses are distributed away from leg openings and a waist opening. U.S. Patent Publication Number 2003/0220626, published on Nov. 27, 2003, describes an absorbent article that does not require a loop fastener as seen in hook and loop type fasteners.

Still other absorbent articles have been described in U.S. Pat. No. 6,520,944, issued to Jonbrink on Feb. 18, 2003 (a diaper); U.S. Patent Publication Number 2003/0229327, published on Dec. 11, 2003 (absorbent pants having high leg cuts); U.S. Patent Publication Number 2003/0164136, published on Sep. 4, 2003 (a wearing article having a wetness indicator); U.S. Patent Publication Number 2003/0149412, published on Aug. 7, 2003 (diaper having permanent leg openings); and U.S. Patent Publication Number 2003/0212378, published on Nov. 13, 2003 (a refastenable absorbent garment having elastic members at a waist opening and leg openings to enhance containment and absorption of body exudates).

None of the above inventions and patents, taken either singly or in combination, is seen to describe the instant invention as claimed. Thus a diaper with legs solving the aforementioned problems is desired.

SUMMARY OF THE INVENTION

The diaper with legs of the present invention is a lower torso garment worn by a user to retain excreted waste matter. The diaper may have fasteners to close the waist and legs, or may be of the pull-on or pull-on type. The diaper includes a flat sheet wrapped around the torso with legs extending from the sides of the sheet. A front waist arch and a rear waist arch are disposed at an upper portion of the edges of the sheet. The arches extend the height of the diaper in front and back. An elastic material is disposed at the waist arches, at the junction between the legs and the central portion of the diaper, and at the end of the legs. The elastic material disposed at the end of the legs and at the junction between the legs and the central portion provides double leak protection at the legs.

These and other features of the present invention will become readily apparent upon consideration of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
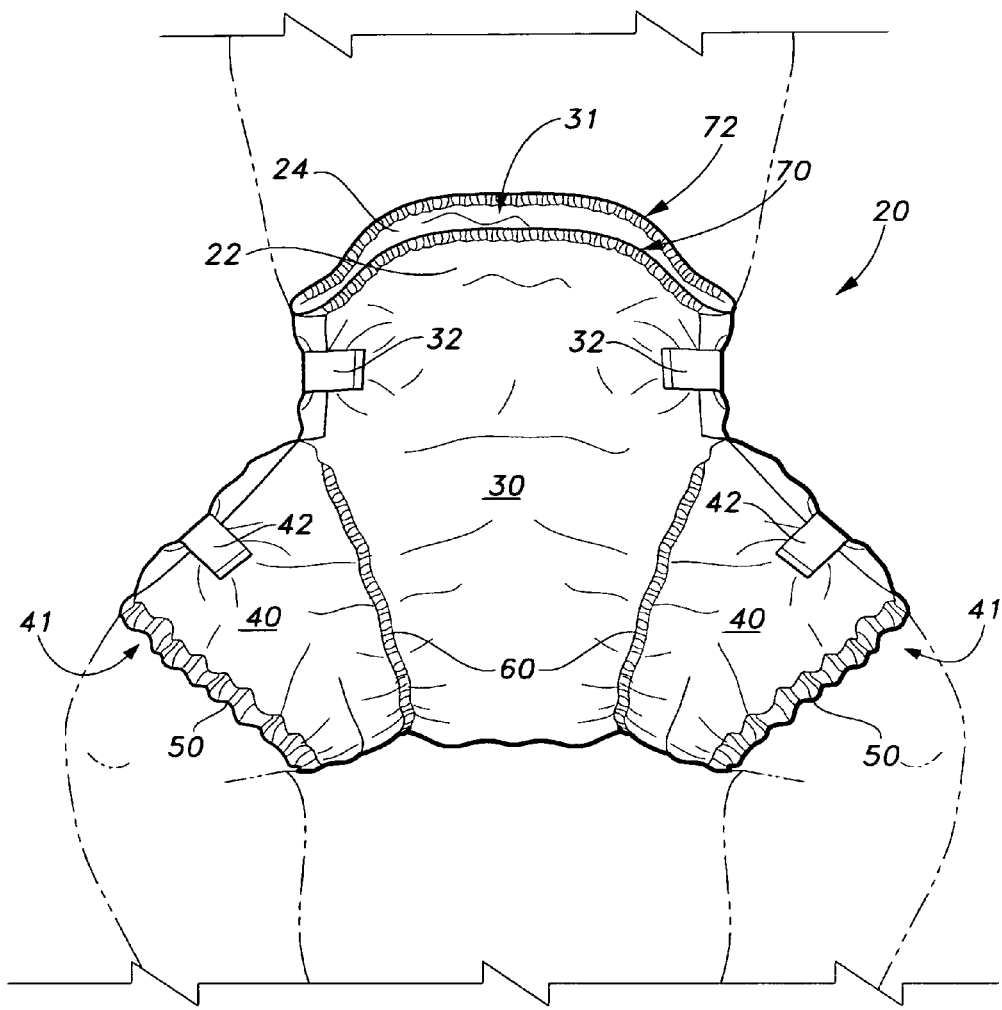
FIG. 1 is an environmental, perspective view of a diaper with legs according to the present invention.

The present invention is a disposable diaper or other garment for babies or others suffering from incontinence. The disposable garment is referred to below as a diaper 20 in FIGS. 1 and 2, but may be scaled up to a garment for adults. The diaper 20 is shown in FIG. 1 in a fastened, closed configuration. The diaper 20 has a central portion 30 and legs 40. The central portion 30 has an upper portion and a lower portion that covers a user's waist and crotch. The lower region of the central portion 30 defines a pair of upper thigh openings. The upper region of the central portion 30 defines a waist opening 31. Specifically, a front waist arch 70 and a rear waist arch 72 extend from the upper region of the central portion 30 and define the waist opening 31. The arches 70, 72 elevate the waist opening 31 so the upper region of the diaper 20 covers a larger area on the user's waist.

The legs 40 downwardly depend from the pair of upper thigh openings disposed at the lower region of the central portion 30. The legs 40 have a top end and a bottom end 50. The top end of the leg sleeve 40 is attached to the central portion by elastic material 60 which defines the upper thigh openings. The bottom end 50 defines leg openings 41 that terminate on the thigh of the user's leg, preferably at about the mid to lower thigh.

The diaper 20 uses elastic material or any other resilient material to provide tight seals and conform to the user's body. For example, elastic material 60, disposed between the legs 40 and the central portion 30, forms a tight seal on the upper thigh of the user. Likewise, the bottom ends 50 of the legs 40 utilize elastic material 60 to form a tight fit on the users mid to lower thigh.

Waste matter excreted by the user is retained within the diaper 20 due to the seal formed at the user's upper thighs by the elastic material 60. If, however, waste matter leaks past the elastic material 60, then the seal provided at the bottom end 50 of the leg sleeves 40 should contain the waist in the leg sleeves 40 and prevent waste matter from leaking out the leg openings 41. Here, the elastic material 60 and the elastic incorporated at the bottom end 50 of the leg sleeves 40 provide double protection from waste matter leaking out the leg openings 41.

The diaper 20 is maintained in the fastened, closed configuration by fastening members 32, 42. Fastening members 32 are disposed on the central portion 30 and fastening members 42 are disposed on the legs 40. The fastening members 32, 42 may be a narrow tab or a wide flap held in place by adhesive or hook and loop material (VELCRO) or any other appropriate known fastener system. At least one pair of both fasteners 32 and fasteners 42 are disposed on the diaper 20 to fasten the diaper 20 and hold it in the closed configuration. Fastener members 32, 42 are made from any reclosable fastening material.

The diaper 20 has an exterior surface and an interior surface. In the closed configuration, the interior surface 24 is dimensioned and configured to contact the user's body, crotch and legs while the exterior surface is designed to contact clothing worn by the user. The exterior surface 22 includes non-absorbent material and is impermeable to liquids. The interior surface 24 of the diaper 20 includes preferably two absorbent materials. The materials are two layers of absorbent liners that are disposed one on top of the other. The absorbent material gives the diaper 20 a maximum thickness of about one-half inch. An inner liner material 25 may be one or more layers of fabric which covers all or part of the interior of the diaper and is made of permeable material which allows urine through to the absorbent material for additional comfort of the wearer. Such liner material is well known in the art and is generally and commercially referred to as a "STAY-DRY" liner or the like which allows exudates to travel through for absorption but minimizes flow or exudates back to the skin of the wearer. Any of the embodiments of the invention described herein may be provided with a similar liner 25.

Figure 2:
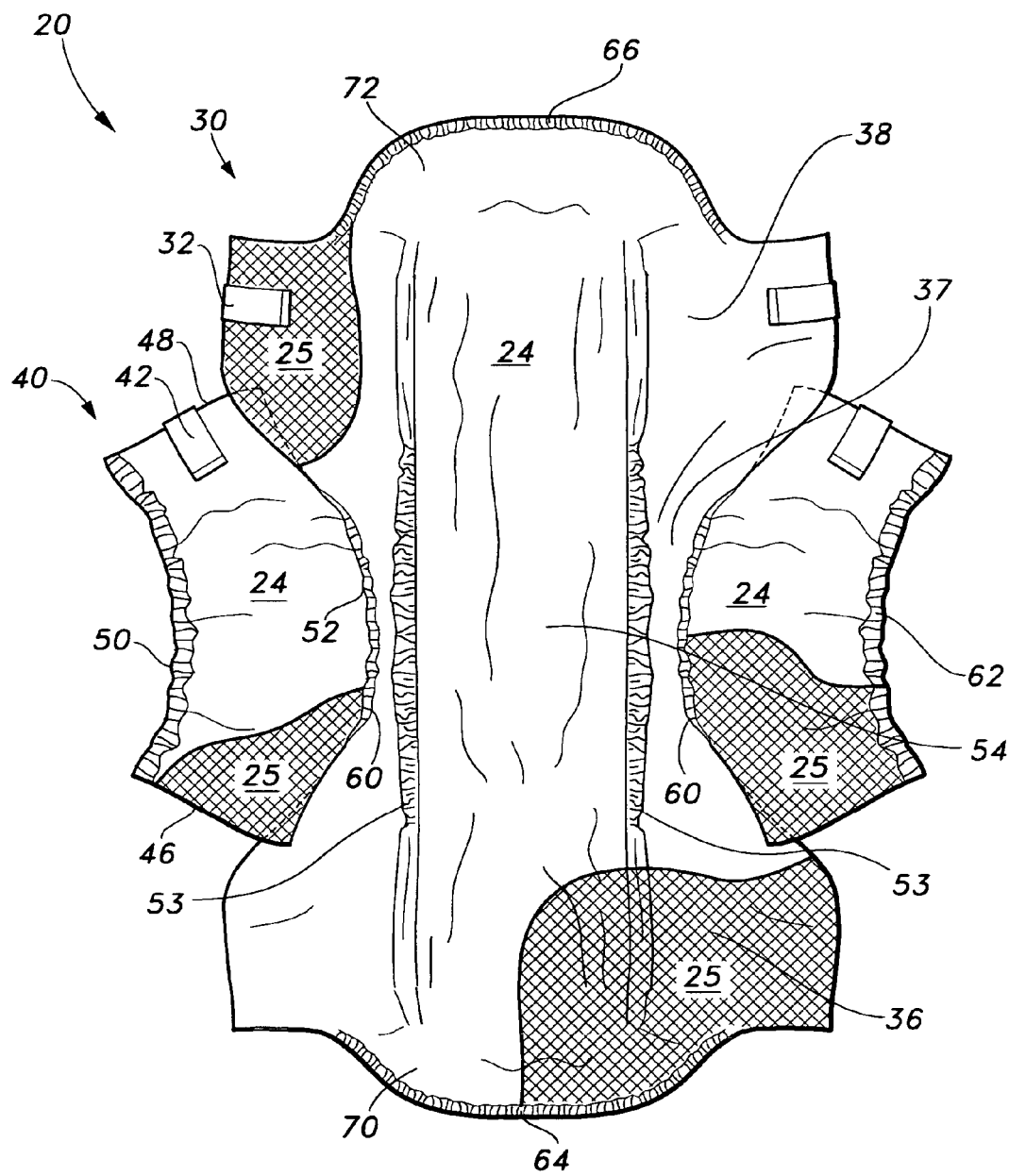
FIG. 2 is a plan view of the diaper with legs according to the present invention in an unfolded state.

Referring now to FIG. 2, the diaper 20 is shown in an open configuration, comprising a sheet with the interior surface 24 of the diaper 20 absorptive material facing upward. The central portion 30 includes a front waist panel 36, a crotch region 37 and a rear waist panel 38 forming a generally hourglass shape. A liner 25 may cover the interior surface 24 as described above.

The front waist arch 70 is formed integrally with the front waist panel 36 and the rear waist arch 72 is formed integrally with the rear waist panel 38. The arches 70, 72 incorporate elastic material (e.g., gathers) 64, 66, respectively, at upper edges of the arches. Like the elastic material 60 disposed between the legs 40 and the central portion 30 and the elastic gathers incorporated at the bottom ends 50 of the legs 40, the elastic material 64, 66 disposed at the upper edges of the arches 70, 72, provides protection from leaks that otherwise would seep up the waist panels 36, 38 and out the waist opening 31.

Waist panels 36, 38, form the wide part of the diaper 20 and the crotch region 37 disposed between the waist panels 36, 38 defines the narrow part of the diaper 20. Fasteners 32 are disposed at the ends of the widest part of the rear waist panel 38. As shown in FIG. 1, the fasteners 32 hold the central portion 30 together in the closed configuration. The crotch region 37 is dimensioned and configured to cover the genitalia of the user. The crotch 37 defines the upper thigh openings of the diaper 20 and is bordered by elastic material 60. Elastic material 60 attaches the legs 40 to the central portion 30 of the diaper 20.

In the open configuration, the legs 40 have a generally rectangular panel shape defined by a rear edge 48, a front edge 46, an inner edge 52 and an outer or bottom end 50. Fasteners 42 are disposed at the rear side 48 of the legs 40 to be refastenably affixable to the front side 46 when the legs 40 are configured around the user's legs. About a central, one-third portion of the length of the top edge 52 of each leg 40 is attached to the central portion 30 by the elastic material 60.

As mentioned above, the interior surface 24 of the diaper 20 is composed of absorbent material. In the central portion 30, the absorbent material is longitudinally arranged at the crotch region 37 to form an absorbent core 54 which is shown as being defined by parallel gathers 53 in the absorptive material. In the legs 40, the absorbent material is disposed within the generally rectangular panel of legs 40 between the rear edge 48, the front edge 46, the inner edge 52 and the bottom end 50.

The liner 25 may be less hydrophilic than the absorbent core 54, to present a relatively dry surface to the wearer, and may be sufficiently porous to be liquid permeable, permitting liquid to readily penetrate through its thickness. Suitable web materials for manufacturing the liner 25 include porous foams, reticulated foams, apertured plastic films, synthetic fibers such as polyester or polypropylene fibers or a combination of natural and synthetic fibers. The liner 25 is employed to help isolate the wearer's skin from liquids held in the absorbent core 54.

The absorbent core 54 may be composed of a matrix of hydrophilic fibers, such as a web of cellulosic fluff, mixed with particles of a high-absorbency material commonly known as superabsorbent material such as superabsorbent hydrogel-forming particles. The superabsorbent particles may be mixed with the hydrophilic fibers. The absorbent inner surface 24 may be woven or unwoven hydrophilic fibers as described above and including natural, synthetic, and modified natural polymers and materials such as cotton or cotton-like material, two or more layers of which may form the absorbent core 54.

The absorbent surface material 24, including absorbent core 54, may contain a wetness indicating composition which assumes a color upon exposure to urine which is visible to an outside observer and so indicating that the need for diaper change is imminent. Such compositions include colorants, such as food grade dyes and pH indicators that change color when wetted with urine. The colorant may also be applied to the inner side of the exterior surface material 22. An example of such a colorant is the acid form of Bromocresol Green, available from Aldrich Chemical Company, Milwaukee, Wis., U.S.A.

In use, a caregiver aligns the user over the interior surface 24 of the open diaper 20 so that the user's back rests on the rear waist panel 38, the user's genitalia align with the crotch region 37, and the user's legs lie in the center of the leg sleeves 40. The diaper 20 is then folded at the crotch region 37 so the front waist panel 36 lies on the user's waist. The fastening members 32, disposed on the rear waist panel 38 can then be attached to the front waist panel 36 to hold the diaper 20 in a closed configuration.

In order to hold the waist panels 36, 38 to the user's body, both panels 36, 38 must be stretched around the user's waist sides so that the fastening members 32 can be fixed to the front waist panel 36. By stretching the panels 36, 38, the elastic materials 64, 66 disposed within the arches 70, 72 are extended and the arches 70, 72 are held taut against the user's body. The arches 70, 72, therefore, create a close fit at the waist opening 31 of the diaper 20 to provide protection against waste matter leaking out of the waist opening 31.

To form the legs 40 and define the leg openings 41, the front edge 46 and the rear edge 48 are brought together and wrapped around the user's leg. Fastening member 42, disposed on the rear edge 48, stretches over and attaches to the front edge 46 forming the legs 40 and the leg openings 41. The top edges 52 of the legs 40 are free to encircle the user's legs, since only the central one-third portion of the top edges 52 are attached to the crotch 37 of the central portion 30. When properly fastened on the user, the legs 40 form a first seal at gathered elastic strip 60 with the user's upper thigh. The outer edges of legs 40 each have an elastic gather 50, forming a second seal with the user's mid thigh. The elastic gathers at 60 and 50 thereby form a double barrier to keep exudates from running down the leg of the user and out of the diaper. The leg fastening member 42 may be adhesive, hook and loop, stretch tab, or other appropriate fastener.

Figure 3:
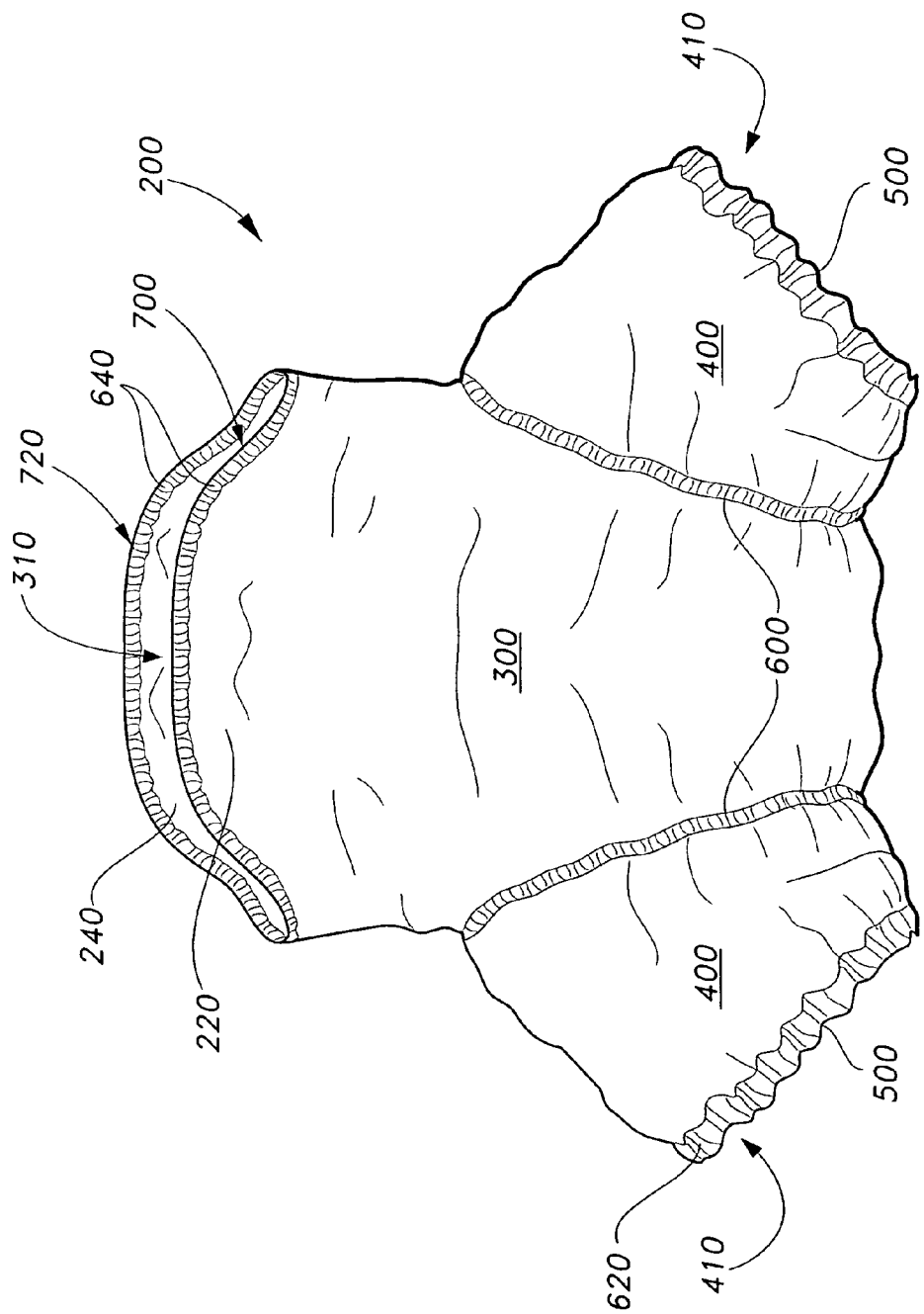
FIG. 3 is a front perspective view of an alternative embodiment of the diaper with legs of the pull-on type.

An alternative embodiment to the diaper 20 is a disposable pull-on diaper 200 shown in FIG. 3. The diaper 200 includes a flexible, absorbent fabric having a central portion 300 having a front, a back, an upper portion defining a waist opening 310 and a lower portion to which a pair of legs 400 are attached. A front waist arch 700 and a rear waist arch 720 are disposed at the upper portion of the diaper 200, further defining the waist opening 310 and extending the coverage of the diaper 200 upward on the waist of the user. Elastic material 640 is incorporated at upper edges of the arches 700, 720 and encircles the waist of the user. The elastic material 640 forms a seal to the user's upper torso to prevent waste matter from seeping up and out the waist opening 310.

Legs 400 have a top end and a bottom end 500. The top end of the legs 400 is fixed to the lower region of the central portion 300 with elastic material 600. The bottom end 500 of the legs 400 terminate at the mid to lower thigh of the user. The legs 400 define leg openings 410. The elastic material 600 disposed between leg sleeves 400 and the central portion 300 forms a first seal, and the elastic gather incorporated at the bottom end 500 of the legs 400 forms a second seal, providing double leak protection against waste matter seeping down the user's leg at the leg openings 410. The diaper 200, like diaper 20, has an absorbent interior surface 240 and a non-absorbent exterior surface 220.

The outer, non-absorbent exterior surface 220 may be of a noon-porous material which repels or stops liquid from entering the interior of the pull-on diaper 200, allowing the diaper 200 to be useful as a swimsuit. Suitable materials for exterior surface 220 may be manufactured from thin plastic film or other suitable flexible liquid-impermeable material. For example, the outer cover 220 may be formed from a polyethylene film. A more cloth-like material includes a polyolefin film having a nonwoven web, such as a spunbond web of polyolefin fibers, laminated to the exterior surface thereof. The exterior surface may be formed of a woven or nonwoven fibrous web layer which has been totally or partially constructed or treated to impart a desired level of liquid impermeability.

The exterior surface 220 may be composed of a microporous breathable material which permits vapors to escape while preventing liquid exudates from passing through which are well known in the art. This material would be most desirable when the diaper is worn under clothing.

The interior surface 240 of the diaper 200, specifically, the central portion 300 and the legs 400, preferably includes two absorbent materials that are disposed on top of each other in layers. A liner (not shown) made of identical material and similar in form to that of FIGS. 1 and 2, elements 25 and described above, may cover the interior absorbent materials having interior surface 240 as desired.

Figure 4:
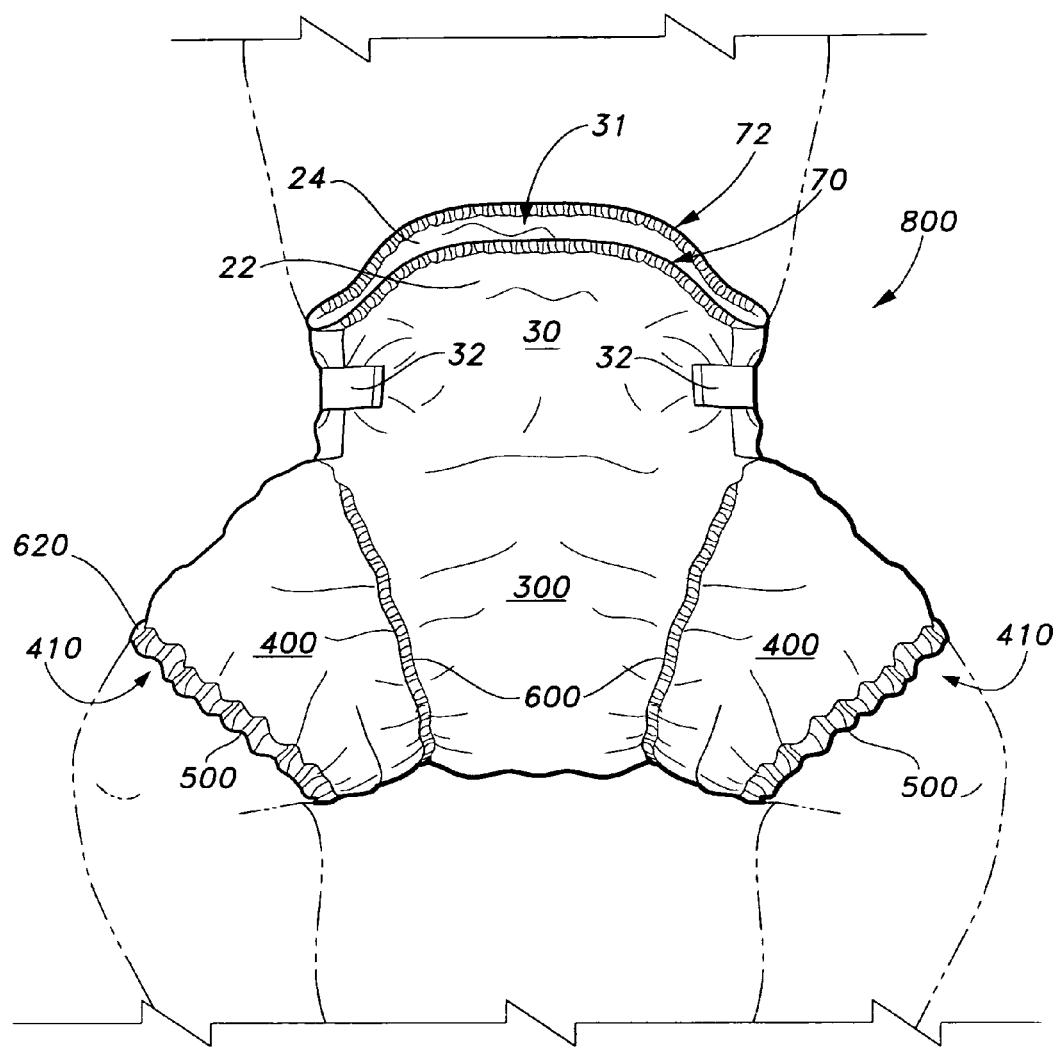
FIG. 4 is an environmental, perspective view of another embodiment of the diaper with legs of the pull-on type and a waist of the fastener type.
Figure 5:
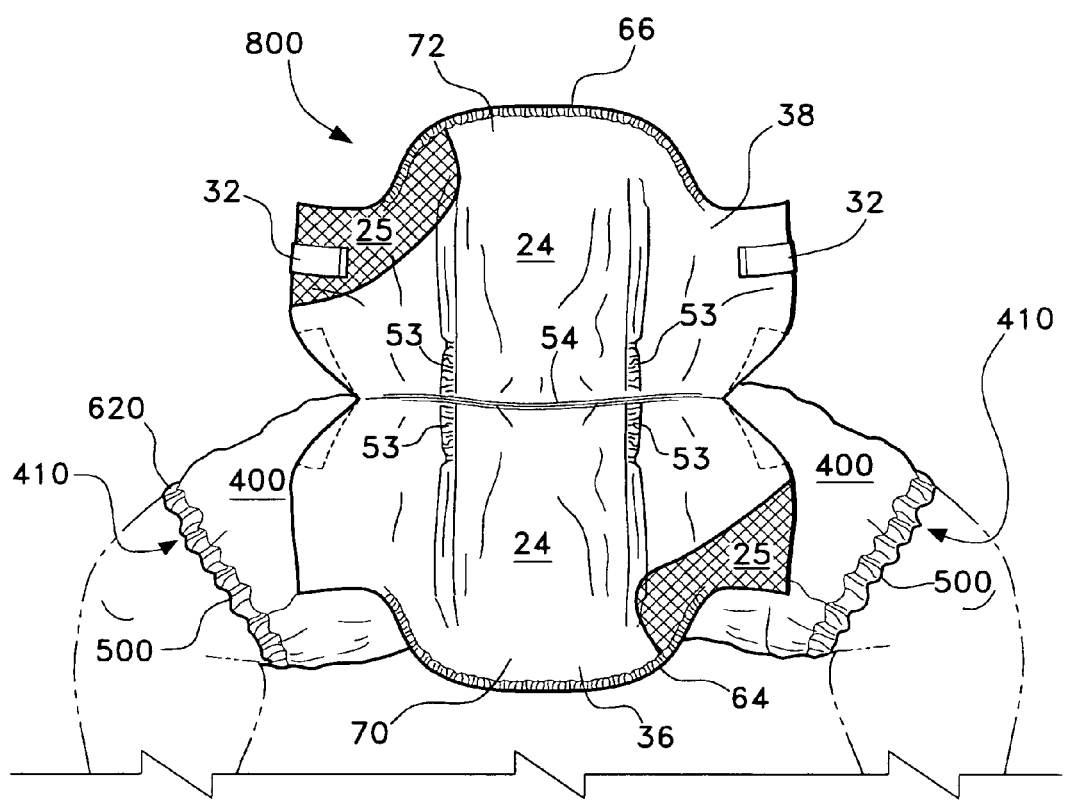
FIG. 5 is an environmental, perspective view of the embodiment of FIG. 4 with the waist open and the front panel folded down.
Figure 6:
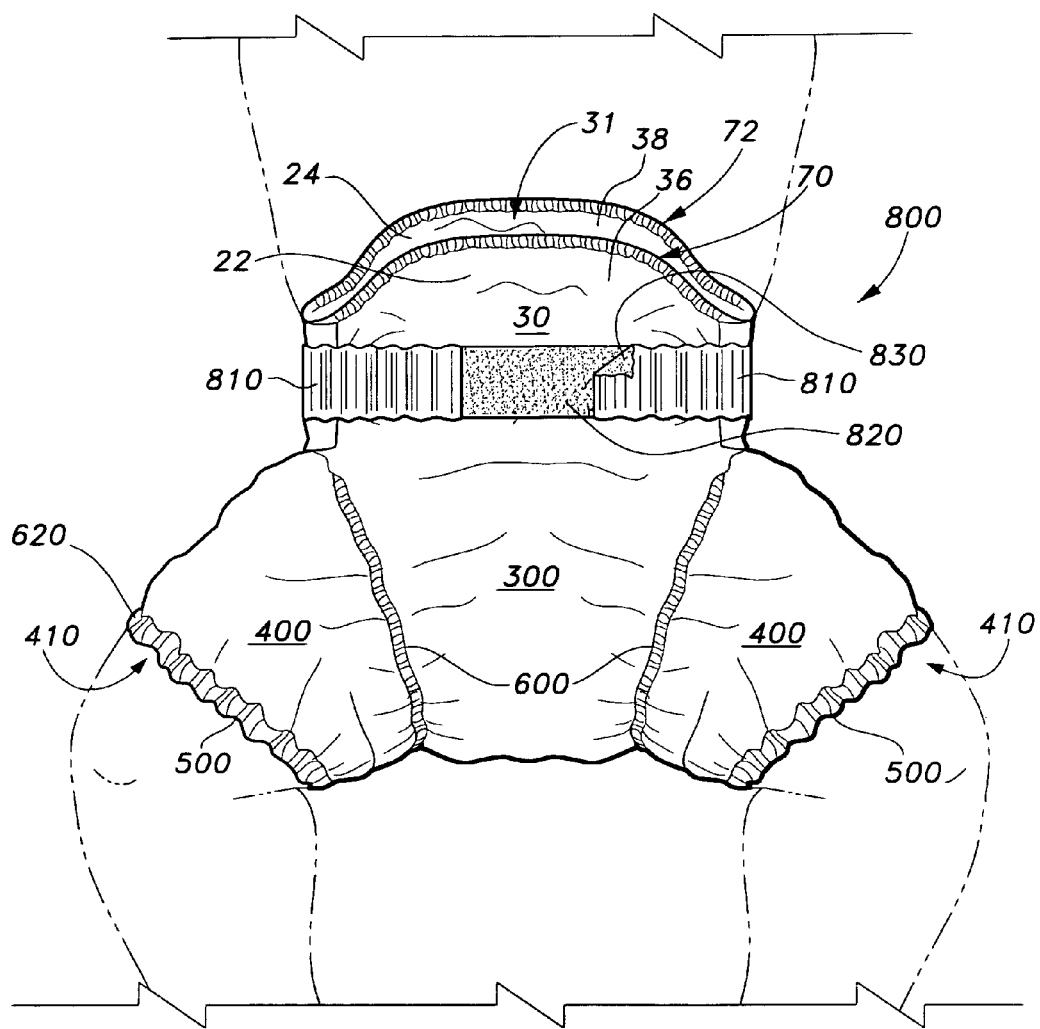
FIG. 6 is an environmental, perspective view of the embodiment of FIG. 4 having fastened hook and loop material stretch tabs.

Referring to FIGS. 4-6, there is shown another embodiment of the present invention referred to as a partial pull-on diaper and combining the pull-on feature of the embodiment of FIG. 3 forming its lower portion and the fastener embodiment of FIGS. 1-2 forming its upper portion and referred herein as a combined pull-on and fastener diaper 800. Diaper 800 has the same features as that of diaper 20 in its upper portion and is configured and fastened in place in an identical manner as that of diaper 20 as described above. The upper central portion 30 has an upper portion that covers a user's waist. The upper region of the central portion 30 defines a waist opening 31. Specifically, a front waist arch 70 and a rear waist arch 72 extend from the upper region of the central portion 30 and define the waist opening 31. The arches 70, 72 elevate the waist opening 31 so the upper region of the diaper 20 covers a larger area on the user's waist.

The diaper 800 uses elastic material or any other resilient material to provide tight seals and conform to the user's body. The diaper 800 is maintained in the fastened, closed configuration by fastening members 32. Fastening members 32 are disposed on the upper central portion 30. The fastening members 32 may have a narrow tab or a wide flap held in place by adhesive or hook and loop material (VELCRO) or any other appropriate known fastener system. At least one pair of fasteners 32 is disposed on the diaper 800 to fasten the diaper 800 and hold it in the closed configuration. Fastener members 32 are preferably made from any reclosable fastening material.

The diaper 800 has an exterior surface and an interior surface. In the closed configuration, the interior surface 24 is dimensioned and configured to contact the user's lower waist area while the exterior surface is designed to contact clothing worn by the user. The exterior surface 22 includes non-absorbent material and is impermeable to liquids. The interior surface 24 of the diaper 800 includes preferably two absorbent materials. The materials are two layers of absorbent liners that are disposed one on top of the other. The absorbent material gives the diaper 20 a maximum thickness of about one-half inch. An inner liner material 25 may be one or more layers of fabric which covers all or part of the interior of the diaper and is made of permeable material which allows urine through to the absorbent material for additional comfort of the wearer. Such liner material is well known in the art and is generally and commercially referred to as a "STAY-DRY" liner or the like which allows exudates to travel through for absorption but minimizes flow or urine back to the skin of the wearer. The liner 25 is further described above in connection with the first two embodiments 20 and 200.

Referring now to FIG. 5, the partial pull-on diaper 800 is shown in an open configuration, comprising a sheet with the interior surface 24 of the diaper 800 absorptive material facing upward. The upper central portion 30 includes a front upper waist panel 36, and a rear waist panel 38 extending upward from lower portion 300. A liner 25 may cover the interior surfaces 24 as described above.

The front waist arch 70 is formed integrally with the front waist panel 36 and the rear waist arch 72 is formed integrally with the rear waist panel 38. The arches 70, 72 incorporate elastic material (e.g., gathers) 64, 66, respectively, at the upper edges of the arches forming a first seal. The elastic material 64, 66 disposed at the upper edges of the arches 70, 72, provides protection from leaks that otherwise would seep up the waist panels 36, 38 and out the waist opening 31.

Waist panels 36, 38, form the wide part of the diaper 800. Fasteners 32 are disposed at the ends of the widest part of the rear waist panel 38. As shown in FIG. 4, the fasteners 32 hold the central upper portion 30 together in the closed configuration.

As mentioned above, the interior surface 24 of the diaper 800 is composed of absorbent material. In the upper central portion 30, the absorbent material is shown having parallel gathers 53 in the absorptive material which extend downward and define a central core 54 within the lower portion of the diaper 800 in the manner of diaper 20 above.

The diaper 800 includes a flexible, absorbent fabric having an upper central portion 30 as described above, attached to a lower central portion 300 having a front, a back, and to which a pair of legs 400 are attached. Legs 400 have a top end and a bottom end 500. The top end of the legs 400 is fixed to the lower region of the central portion 300 with elastic material 600. The bottom or outer end 500 of the legs 400 terminate at the mid to lower thigh of the user. The legs 400 define leg openings 410. The elastic material 600 disposed between leg sleeves 400 and the central portion 300 and the elastic gather incorporated at the bottom end 500 of the legs 400 form first and second seals providing double leak protection against waste matter seeping down the user's leg at the leg openings 410. The diaper 200, like diaper 20, has an absorbent interior surface 24 and a non-absorbent exterior surface 22. The outer, non-absorbent exterior surface 22 may be of a non-porous material which repels or stops liquid from entering the interior of the pull-on diaper 800, allowing the diaper 200 to be useful as a swimsuit. The interior surface 24 of the diaper 800, specifically, the central portion 300 and the legs 400, preferably includes two absorbent materials that are disposed on top of each other in layers. A liner 25 made of identical material and similar in form to that of FIGS. 1 and 2, and described above, may cover the interior absorbent materials having interior surface 24 as desired.

In use, the user pulls up the diaper 800 over his legs. The user or caregiver then reaches back and pulls fastening members 32 and attached rear waist panel 38 forward and attaches them to front waist panel 36 to hold the diaper 800 in a closed configuration for wear. To remove, the fastening members 32 are unfastened from front waist panel 36 and the diaper slid down the legs of the user and over his feet, thus removing the diaper 800.

Referring to FIG. 6, there is shown a diaper 800 having stretch tab fasteners 810 removably fastened to the outer surface of front portion 36. As shown, front portion 36 has a strip of loop material 820 at the waist and stretch tab fasteners 810 have hook material 830 (VELCRO) on their inner side so as to releasably secure stretch tabs 810 to the front portion 36 of diaper 800. Stretch tab fasteners 810 contain elastic to allow them to be pulled tight before attachment to front portion 36 for secure fastening of the diaper 800 on the user.

It is to be understood that the present invention is not limited to the embodiments described above, but encompasses any and all embodiments within the scope of the following claims.

I claim:

1. A diaper with legs, comprising:
    a sheet of material having a central portion defining an interior surface and an exterior surface, a front waist panel, a rear waist panel, and a crotch region connecting said waist panels, said waist panels defining a waist opening, said crotch region defining a pair of thigh openings;
    a pair of leg panels having inner edges attached to respective said thigh openings of said central portion, each of said leg panels having a free outer edge forming a lower edge of each of the diaper legs and defining leg openings that terminate on about the mid to lower thigh of a user's leg;
    elastic material disposed between each said leg panel and at least a portion of respective said thigh openings;
    elastic material disposed at each said free outer edge of said leg panels;
    a front waist arch integral with and extending from said front waist panel and having an upper edge having elastic material incorporated therein; and
    a rear waist arch integral with and extending from the rear waist panel and having an upper edge having elastic material incorporated therein;
    whereby upon mounting said diaper on a user, said elastic material between said leg panels and said thigh openings form a first barrier to leakage of exudates down the user's leg, and said elastic material disposed at said outer edges of said leg panels form a second barrier to leakage of exudates down the user's leg; and
    whereby said front and rear arches form respective barriers to leakage of exudates up the user's waist.

2. The diaper with legs according to claim 1, further comprising at least one pair of fasteners disposed on said rear waist panel for affixing said rear waist panel to said front waist panel.

3. The diaper with legs according to claim 2, wherein each said fastener is an adhesive strip.

4. The diaper with legs according to claim 2, wherein each said fastener includes hook or loop material and said front waist panel has respective mating hoop or loop material, each said fastener including a stretch tab.

5. The diaper with legs according to claim 1, wherein elastic material extends for a central one-third portion of said leg panels and said thigh openings between said leg panels and said thigh openings.

6. The diaper with legs according to claim 1, wherein each of said leg panels comprise a front edge and a rear edge.

7. The diaper with legs according to claim 5, further comprising at least one pair of fasteners disposed on the rear edges of said respective panels for fastening said rear edges to respective said front edges to define said legs.

8. The diaper with legs according to claim 1, further comprising releasable fasteners securing said front waist panel and said rear waist panel, thereby defining said waist opening and securing each said respective leg together.

9. The diaper with legs according to claim 1, said leg panels forming integral legs and wherein elastic material extends about the entire inner edge of each said leg, connecting the entire inner edge of each said leg to the entire edge of respective said thigh openings to form a partial pull-on garment.

10. The diaper with legs according to claim 9, wherein said front waist panel is permanently secured to said rear waist panel in order to form a pull-on diaper.

11. The diaper with legs according to claim 10, wherein said exterior surface is impervious to liquids, thereby making said pull-on diaper useful as a swimming garment without leakage of exudates into the surrounding water.

12. The diaper with legs according to claim 1, further comprising absorbent material disposed between said interior surface of said central portion and each said leg panel and said exterior surface of said central portion and each said leg panel.

13. The diaper with legs according to claim 12, wherein said absorbent material further comprises an absorbent core longitudinally arranged in said central portion.

14. The diaper with legs according to claim 12, wherein said absorbent material comprises at least two layers of absorbent material.

15. The diaper with legs according to claim 13, wherein said absorbent core is formed by spaced parallel gathers.

16. The diaper with legs according to claim 12 wherein said absorbent material contains a wet diaper indicator dye.

17. The diaper with legs according to claim 1, further comprising a wet diaper indicator dye disposed on said exterior surface material.

18. The diaper with legs according to claim 1, wherein said elastic material disposed at each said outer edge of said leg panels comprises an elastic gather.

19. The diaper with legs of claim 1, further comprising a liner of flexible material covering said interior surface material.

20. A pull-on diaper with legs comprising:
    a sheet of material having a central portion defining an interior surface and an exterior surface, a front waist panel, a rear waist panel, and a crotch region connecting said waist panels, said waist panels defining a waist opening, said crotch region defining a pair of thigh openings;
    a pair of legs, each leg having an inner, upper edge and a free outer edge forming the lower edge of said legs and defining leg openings terminating on a user's mid thighs;
    said inner edges of said respective legs being connected to said diaper at said thigh openings by elastic material so as to form a first seal with the upper thighs of a user effective to trap exudates of the user within said diaper;
    said lower edges of said legs having elastic material therearound to form a second seal with the mid thighs of the user to trap exudates passing said first seal of the user within said legs;
    a front waist arch integral with and extending from said front waist panel and having an upper edge having elastic material incorporated therein; and
    a rear waist arch integral with and extending from the rear waist panel and having an upper edge having elastic material incorporated therein;
    whereby upon a user pulling on said diaper, said elastic material between said leg panels and said thigh openings form a first barrier to leakage of exudates down the user's leg, and said elastic material disposed at said outer edges of said leg panels form a second barrier to leakage of exudates down the user's leg; and
    whereby said front and rear arches form respective barriers to leakage of exudates up the user's waist.

21. The diaper of claim 20, further comprising absorbent material disposed between said interior surface of said central portion and each said leg and said exterior surface of said central portion and each said leg.

22. The diaper of claim 21, wherein said absorbent material further comprises an absorbent core longitudinally arranged in said central portion.

23. The diaper of claim 21, wherein said absorbent material comprises at least two layers of absorbent material and wherein said absorbent core is formed by spaced parallel gathers.

24. The diaper of claim 20, wherein said diaper contains a wet diaper indicator dye.

25. The diaper of claim 20, wherein said elastic material connecting said legs to said thigh openings comprises an elastic gather, and each said lower edge of said legs comprises an elastic gather, thereby forming said first and second seals.

26. The diaper of claim 21, further comprising a liner of flexible material covering said absorbent material.

27. The diaper of claim 20, wherein said exterior surface is impervious to liquids, thereby making said pull-on diaper useful as a swimming garment without leakage of exudates into the surrounding water.

28. A partially pull-on diaper with legs comprising;
a sheet of material having a central portion defining an interior surface and an exterior surface, a front waist panel, a rear waist panel, and a crotch region connecting said waist panels, said waist panels defining a waist opening, said crotch region defining a pair of thigh openings;
a pair of legs, each leg having an inner, upper edge and a free outer edge forming the lower edges of said legs to define leg openings terminating on a user's mid thighs;
said inner edges of said respective legs being connected to said diaper at said thigh openings by elastic material so as to form a first seal with the upper thighs of a user effective to trap exudates of the user within said diaper;
said lower edges of said legs having elastic material therearound form a second seal with the mid thighs of the user to trap exudates passing said first seal of the user within said legs;
at least one pair of fasteners disposed on said rear waist panel for fixing said rear waist panel to said front waist panel;
a front waist arch integral with and extending from said front waist panel and having an upper edge having elastic material incorporated therein; and
a rear waist arch integral with and extending from the rear waist panel and having an upper edge having elastic material incorporated therein;
whereby, upon a user pulling on said diaper, said elastic material between said leg panels and said thigh openings form a first barrier to leakage of exudates down the user's leg, and said elastic material disposed at said outer edges of said leg panels form a second barrier to leakage of exudates down the user's leg;
whereby said user or a caregiver fastens said rear waist panel to said front waist panel such that said front and rear arches form respective barriers to leakage of exudates up the user's waist.

29. The diaper of claim 28, further comprising absorbent material disposed between said interior surface of said central portion and each said leg and said exterior surface of said central portion and each said leg.

30. The diaper of claim 29, further comprising a liner of flexible material covering said absorbent material.

* * * * *